United States Patent [19]

Jones et al.

[11] Patent Number: 4,525,452
[45] Date of Patent: Jun. 25, 1985

[54] ENZYME IMMUNOASSAY WITH STEP OF IMMERSING SAMPLE IN DEIONIZED WATER

[75] Inventors: Wendy Jones, Sterling Junction; Bego Gerber, Belmont, both of Mass.

[73] Assignee: BTC Diagnostics Limited Partnership, Cambridge, Mass.

[21] Appl. No.: 460,330

[22] Filed: Jan. 24, 1983

[51] Int. Cl.³ .................... G01N 33/54; C12Q 1/04; C12Q 1/29; C12R 1/36

[52] U.S. Cl. .................................... 435/7; 435/4; 435/29; 435/34; 435/810; 435/871; 436/511; 436/531; 436/808

[58] Field of Search ............... 435/4, 7, 29, 34, 39, 435/188, 810, 28, 871; 436/511, 531, 808, 809

[56] References Cited

U.S. PATENT DOCUMENTS

| | | | |
|---|---|---|---|
| 4,188,371 | 2/1980 | Weetall | 436/511 |
| 4,343,896 | 8/1982 | Wolters et al. | 436/808 |
| 4,376,110 | 3/1983 | David et al. | 436/513 |

FOREIGN PATENT DOCUMENTS 8001972  11/1981  Fed. Rep. of Germany .......... 435/7

OTHER PUBLICATIONS

Kellogg Manual of Clinical Microbiology 2nd ed. 1974 Washington, D.C. pp. 124–125.
Uotila et al., Journal of Immunological Methods vol. 42, No. 1 1981 pp. 11–15.
Voller et al., The Enzyme Linked Immunosorbent Assay (ELDSA), 1979 Dynatech Laboratories Inc. pp. 12–15.

Primary Examiner—Sidney Marantz
Assistant Examiner—William J. Herald
Attorney, Agent, or Firm—Barry D. Josephs; Arthur B. Moore; George E. Kersey

[57] ABSTRACT

Immunoassay detection of bacterial diseases, bacteria, and microorganisms using a deionized water collection medium. The preferred enzyme immunoassay is of particular use in clinical or home testing application for detection of bacteria such as gonococcus, antigens derived from such bacteria, and antibodies against the bacteria. A colorimetric detection technique may be employed using chromogenic solutions containing tetramethylbenzidine or water soluble derivatives of tetramethylbenzidine.

24 Claims, No Drawings

ENZYME IMMUNOASSAY WITH STEP OF IMMERSING SAMPLE IN DEIONIZED WATER

BACKGROUND OF THE INVENTION

1. Field of the Invention

The present invention relates to enzyme immunoassay techniques for clinical or home detection of microorganisms and *Neisseria gonorrohoea*. The invention further relates to the use of specimen collection media and chromogenic substances for the enzyme immunoassay.

2. Description of the Prior Art

Patent application U.S. Ser. No. 410,157 filed Aug. 20, 1982 entitled "Colorimetric Detection of Bindable Substances" by Bego Gerber, Elliott Block, Izak Bahar, Mary Coseo, Cheryl Eaton, Wendy Jones, Patricia Kovac, and John Bruins commonly assigned with the present application contains related and common subject matter.

There are a number of immunoassay techniques in contemporary use for laboratory detection and measurement of antigens or antibodies present within a test sample. Most of these techniques, however, are unsuitable for use outside a laboratory setting because of complexity of the detection equipment and other difficulties inherent in conducting many conventional immunoassay techniques. Thus, there is a need for simple, reliable techniques for use in a clinical setting by a physician or a clinician or which may be readily used by a patient in a home diagnostic immunoassay kit for detection of certain diseases or conditions. It may be desired, for example, to design the immunoassay test kit to detect diseases such as gonorrhea (gonococcus antigen), conditions such as pregnancy (HCG immunogen), exact time of ovulation in women (luteinizing hormone antigen), or any one of a number of specific bacteria and other microorganisms. In order for a diagnostic immunoassay kit to be satisfactory for home use, the kit must be relatively inexpensive, the immunoassay method must be easy to use, reliable, and efficient, and above all must be safe. Additionally, the test method must be of sufficient sensitivity to easily detect the desired antigen in the test sample.

The earliest conventional immunoassay methods for detection and measurement of antigens or antibodies in a test sample are the radioimmunoassay method (RIA) and the fluorescent immunoassay technique (FIA). In the radioimmunoassay method, the antigen or antibody to be detected is either directly or indirectly labelled with radioactive isotope, commonly an isotope of iodine. Although a radioimmunoassay generally exhibits a high degree of sensitivity even for detection of trace amounts of test antigen or antibody, these tests all involve the use of hazardous radioactive materials which require special handling, storage, and disposal. Also, expensive analytical equipment is required, particularly in radioimmunoassay methods which involve the precipitation of immune complexes, which requires detailed analytical recovery techniques. Solid phase radioimmunoassays circumvent the need for detailed analytical recovery required in fhe precipitation method, but require much longer incubation times, typically between 30 to 60 hours. Therefore, in view of the potential hazard involved in handling radioactive material, and the need for expensive detection equipment and long incubation times, the radioimmunoassay method is unsuitable for application to home diagnostic kits.

In the immunofluorescence assay the test antigen or antibody may be labelled directly or indirectly by use of fluorescent dyes (fluorochromes) such as fluorscein and rhodamine which can be coupled to the test antigen or antibodies or their immunocomplexes without destroying their specificity. Such conjugates labelled with fluorescent dye can be visualized in a fluorescence microscope. Major disadvantages of the immunofluorescence method either by the direct or indirect method are firstly the dependence on expensive fluorescence microscopes for detecting the labelled conjugate, and secondly, the acknowledged difficulty in quantifying the test antibody or antigen present in the sample. Therefore, the immunofluorescence assay method is unsuitable for use in connection with home diagnostic kits.

In recent years, the enzyme immunoassay method has received increasing attention from researchers for use in detecting and measuring antibodies or antigen in test samples. The enzyme immunoassay methods involve enzyme labelling of the test antigen or antibody either directly or indirectly by labelling immunocomplexes which bind specifically to the test antigen or antibody and which catalyze reaction with a substrate. Some means is provided for monitoring enzyme activity. For example, in the measurement of the enzyme activity of oxidoreductases, one might monitor the oxidation of a chromogenic substance by a substrate such as hydrogen peroxide. Such so-called colorometric assays are readily adapted to the hometesting environment. When the chromogenic substance oxidizes, it forms a chromophore which exhibits visually discernable color changes.

Typical enzyme immunoassays include competitive EIA for antigens, and an enzyme linked immunosorbent assay (ELISA) which also includes direct and indirect ELISA methods. In the competitive EIA method, antigen labelled with enzyme competes with unlabelled sample antigen for binding to a limited quantity of antibodies which have been adsorbed onto a support medium. Once the amount of bound enzyme labelled antigen has been determined, the amount of sample antigen can be determined by the difference between the total amount of antibody bound to antigen less the amount of antibody bound to labelled antigen.

In enzyme immunoassay methods as known in the prior art, antibodies specific to the test antigen may be first adsorbed in excess amount onto a solid surface such as a plastic well or tube. The test solution containing antigen is then added; the antigen will bind to the adsorbed antibody. The solid phase, that is the phase composed of all material bound to the antibody, is then thoroughly washed to separate unbound components. Further steps are directed toward quantifying the bound antigen. In the double sandwich antibody ELISA method, an enzyme labelled second antibody, preferably having binding sites different from those of the first antibody, is added and reacts with specific determinant sites on the bound antigen. The enzyme labelled second antibody is added in excess to assure that all the antigen present in the solid phase that is bound to the first antibody will also be bound to enzyme labelled second antibody. The enzyme labelled second antibody molecules will bind in a fixed ratio to each antigen molecule depending on the valence, i.e. specific available binding sites, of the antigen for the second antibody. The solid phase is again washed to remove excess second antibody and any other unbound constituents. An enzyme substrate is then added in solution in excess amount, whereby it makes contact with the bound solid phase. For the enzyme horseradish peroxidase, the substrate may typically be composed of a solution of hydrogen peroxide and a chromogenic material.

o-Phenylenediamine (OPD) heretofore has been acknowledged as one of the most sensitive chromogenic substrates available for detection of peroxidase activity. However, OPD produces a yellowish/orange chromophore which although discernible to the unaided eye is nonetheless not a preferred color for a chromophore, since the eye is more sensitive to other colors in the light spectrum such as blue. Other conventional chromogenic compounds having good sensitivity for peroxidase enzyme detection in enzyme linked immunoassays are o-tolidine and ABTS [2,2'-azinodi(3-ethylbenzothiazolinesulfone-6) diammonium salt]. Although o-tolidine and ABTS have been used successfully for detection of a number of specific antigens using ELISA methods, these latter two chromogenic compounds each have less sensitivity than OPD. All of these chromogenic compounds have been reported as soluble and initially colorless, yielding color change upon oxidation with hydrogen peroxide. Typical enzymes that have been used in the enzyme immunoassay methods are horseradish peroxidase, glucose oxidase, $\beta$-D-galactosidase, and alkaline phosphatase. However, since the latter two are found in normal human urine, they are not preferred for use in connection with enzyme immunoassay techniques if they are to be applied in home diagnostic kits. The amount of test antigen present in the solid phase of the double sandwich ELISA method is then directly measurable after the chromogenic substrate has been added, since when there is excess substrate the rate of color change of the chromogen is independent of the substrate concentration and is a function of the total enzyme concentration. The enzyme concentration is a function of the amount of enzyme labelled second antibody, which in turn is a function of the amount of test antigen. Therefore, the rate of color change is a function of the amount of test antigen. The rate of color change can be measured by means of a spectrophotometer if quantification of the amount of test antigen is desired. For use in home diagnostic kits when quantification is not required, the assay should be capable of permitting the user to detect a color change visually which in turn would indicate the presence of a specific antigen in the test sample.

In testing specifically for gonorrhea (*Neisseria gonorrhoea*) the fluorescence immunoassay method, or radioimmunoassay methods are not normally employed since these methods when applied to detection of gonococcus bacteria have been reported to be unreliable or else require the use of expensive microscopes or radiation detection equipment. Such equipment can only be used effectively by highly trained specialists.

Enzyme immunoassay methods have heretofore not been used successfully in diagnosis of gonorrhea because they have lacked sufficient sensitivity to detect the presence of low concentrations of gonococcus often present in infected male or female patients. The lack of sensitivity has been attributed in part to the unavailability of suitable collection medium to adequately desorb the GC cells from the collection swab and simultaneously preserve or increase the antigenic binding sites, and in part due to the unavailability of chromogen of sufficient sensitivity.

In attempts to apply enzyme immunoassay methods to detection of gonorrhea, phosphate buffered saline solutions (PBS) have typically been tried as a collection medium for desorption of gonococcus cells from clinical swabs because of the known preserving effect of this solution on gonococcus antigenic binding sites. However, a collection medium composed of PBS solution does not quickly desorb gonococcus cells from the swab, and only preserves the antigenic binding sites without increasing the total number of exposed antigenic binding sites per cell.

The standard techniques used in testing for gonorrhea have preferably been either the direct Gram staining smear technique which is a preferred technique for males, and culture methods employing a standard agar culture medium for testing women patients.

Although the Gram stained smear technique for testing gonorrhea in male patients by staining a sample urethral exudate with Gram dyes is both quick and inexpensive, it nevertheless is not recognized as a legal and definitive test. Corroboration of the results from Gram staining is typically obtained through culture analysis of the sample. This requires that a culture of the specimen be harvested in an agar medium, such as that supplied in standard Transgrow bottles or through use of standard Thayer-Martin culture medium. These tests must be performed in a $CO_2$ rich environment and cannot be done quickly, but rather require at least about a day or longer incubation time. As a result, the culture techniques are far more time consuming and difficult to perform and are therefore not suited for home diagnostic or quick clinical evaluation. Although a positive from Gram staining of a male smear sample is a basis for diagnosis of gonorrhea subject to corroboration by the culture method, a negative result from Gram staining does not necessarily mean that the patient is free of the disease. In situations where the smear technique gives a negative result, it is particularly prudent that the test be repeated through culture by inoculating a sample specimen on a Thayer-Martin or Transgrow culture medium. Some medical experts require that yet a third test, namely a sugar fermentation test be made in order to absolutely confirm presence or absence of the disease in male patients.

The difficulty in reliably diagnosing gonorrhea in female patients is even greater than diagnosing the disease in male patients. In female patients the use of smear staining by Gram's technique is not a recommended procedure. Rather the preferred method is through culture wherein vaginal or cervical specimens are inoculated on standard agar culture media such as the Transgrow or Thayer-Martin media. The culture techniques as above-described are time consuming in that at least one day's time is typically required to harvest the culture before it is possible to make a diagnosis. Additionally, it is well recognized that the conventional Transgrow or Thayer-Martin culture techniques are not suitable for home diagnostic use but are best performed and monitored in a laboratory by skilled clinicians. Furthermore, it is recognized that diagnosis of the disease can be easily missed in women through the use of the culture methods, since endocervical specimens of infected female patients may have very low concentrations of gonococcus cells particularly during the early stages of the disease. It is well recognized that the culture techniques are unreliable for positively diagnosing the presence of gonorrhea in women during the early stages or latency period of the disease which may span a considerable period of time, from days or even weeks from date of initial infection.

Thus, there is presently no one reliable test available for diagnosing gonorrhea in male and female patients which could be performed in a home diagnostic setting. The tests which are conventionally employed require that they be carried out by skilled clinicians within a laboratory setting, particularly if the test involves the growth of culture in standard culture media, or if the test requires complex microscopic examination as in fluorescence immunoassay methods. Additionally the standard laboratory procedures, particularly those employing culture techniques, require high degree of care in maintaining the sterility of the sample and reagents. The Gram staining smear technique preferred for testing male patients, while a quick and convenient test, unfortunately does not provide the degree of reliability required of a home diagnostic test, since Gram staining may result in a negative and yet the patient could very well be infected. Also, the Gram staining technique has the serious practical disadvantage for application to home diagnostic testing in that additional instrumentation such as a microscope with specialized components is required to determine the results: Enzyme immunoassay methods or other serologic methods for diagnosing gonorrhea have been attempted but have heretofore not been employed successfully since results therefrom can be inconclusive, and such tests are unsuitable for home diagnostic study.

Conventional chromogenic reagents preferably are prepared in fresh batches just prior to use, and tend to oxidize and become colored spontaneously when left in storage, typically even for as little as one hour. In general, a chromogenic compound for detection of enzymes such as horseradish peroxidase should be relatively inexpensive, easy to use in connection with home diagnostic assays, and above all, noncarcinogenic and safe. The chromogenic compound importantly should be stable, soluble, and exhibit rapid color change upon reaction. Also, with substrate, e.g., hydrogen peroxide when exposed to oxidative enzymes, the product chromophore should likewise be safe, stable, and exhibit a high molar absorptivity.

Other chromogenic compounds have been used in pathological studies or assays outside the realm of enzyme immunoassay methods. For example, benzidine has been used to determine peroxidase activity of heme proteins. In such an application, benzidine-hydrogen peroxide chromogenic substrates have been used in forensic medicine for the detection of blood using the peroxidase activity of hemoglobin. Also, benzidine staining procedures have been used to detect the peroxidase activity of the heme proteins cytochrome P-450 and cytochrome P-420. Specifically, the peroxidase activity of these cytochromes has been detected on sodium dodecyl sulfate (SDS)-polyacrylamide-gel electrophoresis by a benzidine staining procedure. Problems have been encountered, however, with the use of benzidine, one of the more important being that it has been found to be a potent human bladder carcinogen. Additionally, staining with benzidine may lack sensitivity. The stain exhibits limited stability, therefore making it difficult to photograph. Researchers in the field of forensic medicine have, therefore, sought alternatives to benzidine for the detection of peroxidase activity of heme proteins, in particular for detection of peroxidase activity of hemoglobin. One such alternative reported in the literature is the use of 3,3',5,5'-tetramethylbenzidine in hydrogen peroxide as a stain for the peroxidase activity of heme proteins, particulary cytochrome P-450. The results of the improved staining procedures using tetramethylbenzidine are reported in P. Thomas, B. Ryan, and W. Levin, *Analytical Biochemistry* 75, 168–176 (1976).

The advantages of using tetramethylbenzidine for the heme staining of cytochrome P-450 as reported in this reference were that the TMB substrates exhibited increased sensitivity, clear dull background, thereby improving color contrast, and greater staining stability, i.e., the TMB stained gels could be stored in the dark at room temperature for at least one month with only minimal loss in TMB stain intensity. In Thomas et al. supra., the improvement in stability of the TMB-hydrogen peroxide staining was reported to be in marked contrast to that obtained with benzidine-hydrogen peroxide where much of the stain is lost within one hour after heme staining for detection of cytochrome P-450. The TMB stained gels were reported to give distinct color even after 25 hours, in contrast to the results obtained with benzidine heme staining wherein much of the color was lost in only one hour after staining.

In the reference Thomas et al. supra., the preferred preparation of the TMB chromogenic solution for detecting the peroxidase activity of cytochrome P-450 on sodium dodecyl sulfate (SDS)-polyacrylamide gel was described as follows: A 6.3 mM TMB solution was freshly prepared in methanol. Immediately before use, 3 parts of the TMB solution were mixed with 7 parts of 0.25 M sodium acetate buffer (pH 5.0). After 1 or 2 hours with occasional mixing (every 10–15 min.), $H_2O_2$ was added to a final concentration of 30 mM. The staining was visible within 3 minutes when using this solution. After the gels were stained, they were placed in an acetate buffered 30 percent isopropanol solution (i.e. the gels were placed in isopropanol: 0.25 M sodium acetate, pH 5.0 at a ratio of 3:7). This served to clear the gel background and enhance staining intensity and permitted storage of the stained gels in the dark at room temperature for at least 2 months with minimal loss in stain intensity.

The use of alternative solvents for TMB such as ethanol or isopropanol instead of methanol reportedly resulted in diminished stain intensity. The 3:7 ratio of methanol to sodium acetate buffer of pH 5.0 was found to be optimal. When the pH 5.0 sodium acetate buffer was replaced with buffers at pH 4.0, 4.5, 5.5 or 6.0, the stability and sensitivity of staining were significantly reduced.

A salt of tetramethylbenzidine, believed to be noncarcinogenic, namely tetramethylbenzidine dihydrochloride (TMB-d) has been reported in the literature and used as a suitable substitute for benzidine for staining of hemoglobin containing cells and for quantitative determination of hemoglobin in solutions. See, H. H. Liem, et al. *Analytical Biochemistry*, 98, 388–393 (1979). Unlike tetramethylbenzidine, TMB-d is water soluble obviating use of an organic solvent. It also dissolves in 10 percent acetic acid forming a green oxidation product. It has the disadvantage, however, of being unstable in the presence of moisture and air, thereby diminishing its effectiveness.

The use of tetramethylbenzidine-hydrogen peroxide chromogenic substrates as stains for detection of peroxidase activity of heme proteins, such as cytochromes, as reported in Thomas et al., or hemoglobin as reported in Liem is directed to the forensic sciences for detection of blood particularly in samples produced during criminal or accident investigations. The uses of tetramethylbenzidine disclosed in these references, including heme staining and staining of cytochrome or hemoglobulin for application to the forensic sciences, do not extend to the use as a chromogen in enzyme immunoassays.

Accordingly, it is an object of the present invention to provide an enzyme immunoassay test which is reliable for detection of microorganisms, antigens derived from microorganisms, and antibodies directed against the microorganisms.

It is an important object of the present invention to provide an enzyme immunoassay technique for gonorrhoea which may be performed by the patient in a home diagnostic study.

It is another important object of the invention to provide an improved collection medium for the test specimen. A related object of the invention is to provide an enzyme immunoassay test for gonorrhoea incorporating both an improved collection medium and improved chromogenic substrate.

SUMMARY OF THE INVENTION

In accomplishing the foregoing and related objects, the invention provides an improved immunoassay method for detection of bacterial diseases, bacteria or microorganisms, or antibody directed against such bacteria and microorganisms. A preferred immunoassay method is an enzyme immunoassay characterized by the separation of the assay material into solution phase and solid phase components, e.g. of the ELISA type. The enzyme immunoassay is typically carried out as a colorimetric assay involving color change of a chromogenic compound used in the assay.

The invention encompasses an improved enzyme immunoassay which utilizes an improved collection medium for the sample specimen. The improved collection medium is suitable generally for collecting specimen suspected of containing the bacteria or microorganisms being assayed. The collection medium is particularly suitable for collecting sample specimen suspected of containing gonococcus bacteria. The collection medium is employed preparatory to conducting the immunoassay for detection of the gonococcus cells in the sample.

The improved enzyme immunoassay and improved collection medium is thus particularly suitable for desorbing gonococcus cells from urogenital (male) or endocervical (female) samples collected on conventional clinical swabs such as those composed of calcium alginate, compacted cotton, or equivalent material. Surprisingly, it has been determined that a collection medium composed of deionized water, preferably highly deionized water functions to desorb gonococcus cells at high rates from the swab, and also it is theorized increases the total number of exposed antigenic binding sites per cell. Thus, it has been determined that deionized water provides a highly desirable collection medium for desorption of gonococcus cells prior to subjecting the sample to assay by the enzyme immunoassay technique of the invention. Although deionized water such as distilled water gives improved results over conventional collection media such as phosphate buffered saline solution, water deionized to high purity typically having a resistivity between about 1.0 to 20 megaohm cm, more preferably between about 10 and 20 megaohm cm (prior to reabsorption of carbon dioxide from the air) provides a surprisingly effective collection media for gonococcus swab sample.

The clinical swab containing the gonococcus sample is immersed in the deionized water for a minimum immersion period. To complete the collection phase a phosphate buffered saline solution, calcium and magnesium free, is advantageously added to the deionized water at the end of the immersion period of the swab sample therein. The phosphate buffered saline solution may contain a detergent active agent such as polyoxyethylenesorbitanmonolaureate. The collection medium of the invention applied to enzyme immunoassay methods for detection of gonococcus or other bacteria or microorganisms, particularly as applied to a double antibody sandwich enzyme immunoassay is believed to have a combination of properties which increases the rate of desorption of the gonococcus cells (or other bacterial cells being assayed), and also increases the number of exposed antigenic binding sites per cell. Thus, its use in the collection of sample contributes to the overall sensitivity of the enzyme immunoassay technique for home or clinical diagnosis of gonorrhea or other bacterial diseases in male or female patients.

The colorimetric assays of the preferred embodiment utilize a chromogenic substrate such as tetramethylbenzidine or water soluble chemical derivatives of tetrametbylbenzidine. The preferred tetramethylbenzidine is 3,3',5,5'-tetramethylbenzidine and preferred derivatives are water soluble inorganic acid salts of 3,3',5,5'-tetramethylbenzidine, particularly sulphated 3,3',5,5'-tetramethylbenzidine which is the reaction product of concentrated sulfuric acid and tetramethylbenzidine. Another suitable water soluble salt, but somewhat less preferred, is 3,3',5,5'-tetramethylbenzidine dihydrochloride.

It has been determined that tetramethylbenzidine and water soluble derivatives thereof, particularly sulfated 3,3',5,5'-tetramethylbenzidine, exhibit exceptional chromogenic sensitivity and stability making these compounds especially suitable for use in home diagnostic enzyme linked immunoassay methods. TMB possesses superior characteristics as compared with conventional enzyme immunoassay chromogens, providing enhanced sensitivity, with reduced background.

The chromogenic substrates of the invention have been successfully tested in a variety of enzyme immunoassays. They have been found particularly successful in a double antibody sandwich enzyme linked immunoassay method, which is well suited to home diagnostic tests for positive detection of gonococcus (GC) microorganisms. The double antibody sandwich enzyme linked immunoassay method incorporating the chromogenic substance of the invention has the additional advantage that it may be used in clinical or laboratory application for quantitative measurement of gonococcus concentration.

The invention also encompasses the use of activated solutions containing organic or inorganic acid salts of tetramethylbenzidine (TMB solution), particularly an activated solution containing sulfated tetramethylbenzidine (TMB-S). The activated solutions contain the TMB component, solvent, buffer, and hydrogen peroxide. A preferred buffer which enhances the stability of the activated solutions is composed of citrate phosphate dissolved in water, having a pH of about 5.0. When the activated solution contains tetramethylbenzidine, the preferred solvent is methanol; however, an activated solution containing instead a water soluble salt of tetramethylbenzidine, such as sulfated tetramethylbenzidine, has an advantage in that it avoids the need for solvents other than water.

The method of the invention when applied in at-home use employs a solid support surface on which the enzyme linked immunoassay is performed. Preliminary assay stages, such as antibody coating of the solid support and blocking of the support surface to prevent nonspecific binding, may be performed in advance of the at-home assay. The improved enzyme immunoassays of the invention combine high sensitivity and reliability, without requiring an involved or time-consuming procedure.

DETAILED DESCRIPTION

Assay methods applicable in the context of the invention may be, generally, immunoassay methods for detection of bacterial diseases, bacteria or microorganisms, or antibody directed against such bacteria or microorganisms. A preferred immunoassay is an enzyme immunoassay which may be effected as a homogeneous assay or an enzyme immunoassay characterized by the separation of the assay material into solution phase and solid phase components, e.g. an assay of the ELISA type "enzyme linked immunosorbent assay". The enzyme immunoassay is advantageously carried out as a colorimetric assay involving color change of a chromogenic compound used in the assay. Various enzyme linked immunosorbent assay methods which may be conducted using the techniques of the present invention are illustrated in A. Voller, et al., "The Enzyme Linked Immunosorbent Assay", Dynatech Laboratories, Inc., Alexandria, Va. (1979) pp. 1–125. These include competitive, direct and indirect, and inhibition immunoassay techniques. The preferred enzyme immunoassay is an ELISA immunoassay using a double antibody sandwich, discussed generally by Voller at pages 13–15.

The technique and collection medium of the invention may be used advantageously generally for detection of bacterial diseases, bacteria, microorganisms, and antibody directed against the bacteria or microorganisms. The assay technique and collection medium of the invention, for example, may be used advantageously for the detection of the following disease bearing bacteria: Gonococcus, *Streptococcus viridans*, Chlamydia, Salmonella, *E. coli, Vibrio cholerae, H. influenzae* type B and *Streptococcus pneumoniae*. The foregoing list is merely illustrative of possible applicability of specific bacteria for detection with the assay technique and collection medium of the invention, and the invention is not intended to be limited thereto. Although the technique may be used advantageously generally for detection of specific bacteria and other microorganisms, the invention is particularly useful when the assay is directed towards detection of gonococcus bacteria.

In the preferred immunoassay, which is an enzyme immunoassay, an important aspect of the invention is the manner of indexing enzyme concentration, which involves a colorimetric technique. In order to detect the gonococcus antigen or other specific bacteria or microorganism being assayed, the enzyme immunoassay employs the immunochemical reaction of the assayed substance with one or more antibodies labelled with enzymes. The assay method permits the concentration of gonococcus antigen or other specific bacteria or microorganism being assayed to be determined from enzyme concentration. The enzyme concentration is determined by monitoring the rate of reaction of the chromogenic substrate producing chromophores. The reaction rate in turn is measurable by monitoring the rate of color change caused by the chromophores. The assay of the invention is preferably performed in a manner that permits proportional indexing between rate of color change and enzyme concentration.

A preferred embodiment of the invention for detection of gonococcus cells encompasses an improved enzyme immunoassay method of the ELISA type which utilizes an improved collection medium for desorbing gonococcus cells from urogenital (male) or endocervical (female) samples collected on conventional clinical swabs such as those composed of calcium alginate or equivalent material. It has been determined that a collection medium composed of deionized water, preferably highly deionized water functions to desorb gonococcus cells at high rates from the swab. It is theorized that the deionized water also increases the total number of exposed antigenic binding sites per cell. The use of deionized water collection medium therefore increases the overall sensitivity of the enzyme immunoassay method for detection of gonococcus cells in the sample.

It is not known with certainty why the deionized water increases the number of available antigenic binding sites per gonococcus cell. It is theorized that this result may be due in measure to the deionized water's ability to quickly breakdown the calcium and magnesium ion matrix which holds antigenic material bound to the cell surface. As the calcium and magnesium matrix breaks down, antigenic material may be entirely freed from the surface of the gonococcus cell, and thus more able to bind to specific antibody in the enzyme immunoassay.

The deionized water may in part also cause the cell to rupture because of the higher osmotic pressure (hypertonic) of the water in comparison to the intracellular osmotic pressure. If some cells rupture, antigenic material held within the cell membrane may become exposed and provide additional binding sites for specific antibody used in the enzyme immunoassay. Use of the deionized water also results in an increase in rate of desorption of gonococcus cells from the swab. The mechanism for this increase in desorption rate is not entirely understood, but is believed to be in part due to the increased solubilizing effect of the deionized water on the alginate swab itself and/or on the gonococcus cells adsorbed onto the swab surface.

The improved sensitivity of the deionized water over conventional collection medium such as Dulbecco's phosphate buffered saline can be observed when the enzyme immunoassay for gonococcus is performed with the swab sample immersed in deionized water for as little as about 15 minutes prior to conducting the assay. The minimum immersion time suitable for conducting the assay has been determined to depend also on the swab type used. Although calcium alginate swabs may be commonly used, a suitable minimum immersion time of as little as about 15 minutes is more readily obtainable when the swabs are composed of compacted cotton such as that available under the tradename PERNASAL cotton swabs from the Medical Wire and Equipment Co., Cleveland, Ohio. When calcium alginate swabs are used, the minimum required immersion time tends to be higher, typically from about 15 minutes to about 3 to 4 hours.

Although deionized water such as distilled water having a resistivity of at least 1.0 megaohm cm gives improved results, water deionized to high purity, preferably that of reagent grade water having a resistivity of at least 10 megaohm cm and typically between about 10 to 20 megaohm cm (prior to reabsorption of carbon dioxide from the air) provides a surprisingly effective collection medium for gonococcus swab sample. The most desirable highly deionized water is that meeting the standards for Type 1 Reagent Grade Water as set forth by the College of American Pathologists (CAP) or ASTM Standard D-1193. For Type 1 Reagent Grade Water the CAP requires a resistivity of at least 10 megaohm cm, and the ASTM standard requires a resistivity of at least 16.7 megaohm cm. The Type I water by either standard should also be free of particulate matter less than 0.2 micron to remove all bacteria; i.e. less than 500 particles per liter which are greater than 0.2 micron. This highly deionized and purified water can be conveniently produced through use of a mixed bed anion and cation exchanger such as the NANOpure II water purification system available from the Barnstead Company, Division of Sybron Corp. Boston, Mass. The mixed bed exchanger replaces cations with hydrogen ions and anions with hydroxyl ions. The NANOpure system is capable of achieving deionization of up to a level of 18 megaohm cm resistivity and also removes free chlorine and organic hydrocarbons having molecular weight greater than 200. The NANOpure II system includes a filter which removes bacteria and particulate matter larger than 0.2 micron, and removes total matter to a level of less than 0.1 mg per liter.

After the swab sample has been immersed in the deionized water collection medium for the requisite duration, phosphate buffered saline (PBS) or more preferably a PBS/Tween Solution may be added at the start of the assay. The use of a PBS solution at the start of the assay assures that binding of antibody and antigen in the solid phase will occur at suitable pH to assure that the reactivity of the antigen-antibody binding sites is close to optimal. The PBS solution composition may be adjusted accordingly.

The preferred phosphate buffered saline should be essentially free of calcium ions and more preferably free of both calcium and magnesium ions. A detergent active component such as Tween-20 is preferably added to the phosphate buffered saline during preparation to form a PBS/Tween solution. A preferred formulation for the PBS/Tween is essentially free of calcium and magnesium ions and may contain only potassium phosphate, sodium chloride and Tween. A preferred composition of the PBS/Tween is such that the composition of the deionized water after addition of PBS/Tween is as follows:

Potassium Phosphate . . . 0.05 moles per liter
Sodium Chloride . . . 0.5 moles per liter
Tween - 20 . . . 0.1% by volume The pH of the above solution is approximately 8.0.

Chromogenic substrates which contain 3,3′,5,5′-tetramethylbenzidine and its derivatices will provide the required chromogenic sensitivity and reliability of the immunoassay. Of special utility are the water soluble derivatives of TMB, particularly, water soluble organic and inorganic acid salts. Preferred water soluble derivatives of tetramethylbenzidine suitable for enzyme immunoassays include 3,3′,5,5′ tetramethylbenzidine dihydrochloride (TMB-d) and sulfated tetramethylbenzidine (TMB-S). Sulfated tetramethylbenzidine is somewhat more stable than solid tetramethylbenzidine dihydrochloride which has some tendency to oxidize under ambient conditions. Thus, a solution of sulfated tetramethylbenzidine is an especially suitable chromogen for enzyme immunoassays, particularly as applied to home diagnostic methods. All of these compounds have the further advantage of being noncarcinogenic. Chromogens in this family (hydrogen donors) yield distinctive blue chromophores in the presence of hydrogen peroxide (hydrogen acceptor) and an enzyme such as horseradish peroxidase. Horseradish peroxidase catalyzes the decomposition of the enzyme substrate hydrogen peroxide, the product of which causes the partial oxidation of tetramethylbenzidine to produce blue chromophores. This reaction is characterized by a high extinction coefficient, i.e. dense color per TMB molecule degraded.

Applicants have determined that tetramethylbenzidine and its derivatives, particularly sulfated tetramethylbenzidine, are used most advantageously as enzyme chromogenic substrates for home detection or clinical measurement of antigens, e.g. gonococcus, when employed in the direct, double antibody sandwich ELISA method. In application for detection of *Neisseria gonorrhoea,* the user may register the presence of gonococcus qualitatively simply by observing the presence of blue color in an immunoassay sample containing even trace amounts of the subject gonococcus antigen. This subjective observation may be assessed quantitatively as "positive" when the absorbance or optical density at the maximum absorbance wavelength (in the range 620-700 nm for TMB) exceeds a predetermined threshold level nominally on the order of two standard deviations above a negative threshold, illustratively about 0.04. Thus, the method of the invention may be employed in clinical analysis to obtain quantitative measurement of a gonococcus antigen in the test sample. Quantitative measurement is obtained spectrophotometrically by reading the absorbance at maximum absorbance wavelength.

Tetramethylbenzidine and its water soluble chemical derivatives, particularly water soluble inorganic or organic acid salts thereof have important advantages over other sensitive chromogens in application to colorimetric enzyme immunoassays. An activated chromogen solution of o-phenylenediamine (OPD) dissolved in hydrogen peroxide shows the characteristic that the OPD chromogen slowly oxidizes to a yellow/orange color when left to stand alone without the presence of enzyme. This must be taken into account when actually conducting the assay in the presence of enzyme. By contrast, solutions of tetramethylbenzidine in hydrogen peroxide or inorganic or organic water soluble salts of tetramethylbenzidine in hydrogen peroxide oxidize to color far less rapidly than the OPD hydrogen peroxide solution. Therefore, there is significantly less background color development in the case of TMB in hydrogen peroxide. Furthermore, solutions of tetramethylbenzidine or its water soluble salts have the additional advantage over OPD solutions in that the TMB solutions are very stable when left alone prior to admixture of hydrogen peroxide, whereas OPD has the tendency to oxidize slowly even when in water solution. Tetramethylbenzidine or water soluble salts thereof have been determined to be significantly more sensitive chromogens than OPD for use in colorimetric enzyme immunoassays. The chromogenic sensitivity of tetramethylbenzidine or its water soluble salts in hydrogen peroxide, as measured by change in absorbance at wavelength of maximum absorbance, is at least three times greater than for OPD chromogen in hydrogen peroxide wherein each chromogen is exposed to the same enzyme concentration and each chromogen is in the optimal concentration of hydrogen peroxide.

Illustrative TMB solutions for enzyme immunosorptive assays are produced as set forth in Examples 1 and 2 below. The following general conditions apply to the formulation of a suitable chromogen solution. The activated TMB solution should have the maximum amount of TMB chromogen which may be dissolved therein without causing turbidity. If excess chromogen is present the resulting turbidity makes it difficult to read the color intensity of the chromophores spectrophotometrically because of a light scattering effect. Excess organic solvent should be avoided, since such excess could inhibit enzyme activity. In addition, the organic solvent should be within a range to provide satisfactory production of the desired chromophore. Methanol is a preferred organic solvent for such assays.

The principal function of the buffer is to delimit the pH of the activated solution to a range of maximum enzyme activity. Advantageously, the pH range should be between about 4 and 8; more preferably, between about 5 and 6. A suitable buffer pH will depend on the choice of enzyme and the presence of any modifier molecule, as discussed below. The composition of the buffer solution has not been found critical to the present invention, subject to the above constraints.

All water-soluble chromogenic compounds with TMB, such as water soluble acid salts of TMB, are preferred since the use of organic solvents has disadvantages. Most organic water-miscible solvents evaporate easily, thus exposing the user to potential health hazards since many of these solvents are toxic. Solvent evaporation can furthermore cause solution turbidity and deleteriously affect color development. The substrate content (including hydrogen peroxide, in the preferred embodiment) in the chromogen solution should preferably be sufficiently high to saturate the enzyme upon reaction, although hydrogen peroxide may be included in lesser amounts. It is preferred that a saturation quantity of hydrogen peroxide be included in order that the initial rate of color development be directly proportional to enzyme concentration. However, excess hydrogen peroxide should be avoided since it will inhibit enzyme activity. In quantitative measurements of color development, it is advisable to utilize the initial reaction period, during which enzyme activity is most linearly related to enzyme concentration. Measurement may also be made by an end point appraisal after a prescribed reaction period. Although hydrogen peroxide is the preferred enzyme substrate for use with peroxidase, it should be appreciated that other organic peroxides, such as hydroperoxides, may be used which exhibit sufficient specificity for the enzyme particularly methyl hydroperoxide, ethyl hydroperoxide, urea peroxide, or mixtures thereof.

In application of the assay method of the invention for home diagnostic use it is advantageous that the hydrogen peroxide be premixed with the buffer in a first solution and the TMB component premixed with the solvent in a second solution. The user then need only mix these solutions to form the activated TMB solution.

It is desirable to utilize antibodies of high specificity for the antigen, e.g. gonococcus, being assayed. In this regard, the use of multispecific systems may decrease assay sensitivity. A preferred source of monospecific antibodies for such assays is found in the hybridoma technique.

In the preferred embodiment of solid phase immunoassay the various assay components are separated between free, solution phase components, and insoluble components bound to solid carriers such as polypropylene tubes, nylon beads, polystyrene microtiter plates, etc. The immunochemically-active components may be covalently bonded to the solid support, cross linked, or physically coupled thereto. For example, in the double-antibody-sandwich assay illustrated in Examples 6 and 7, a first antibody is adsorbed to the solid support; the test solution containing suspected antigen, e.g. gonococcus, is incubated with the sensitized solid support to effect binding of the antigen to the first antibody; an enzyme labelled second antibody specific to the antigen is then incubated with the solid support to effect binding of the enzyme labelled second antibody to the antigen; and finally the substrate added to test for color change of the solid phase. Incubation of the test antigen is preferably performed simultaneously with incubation of the enzyme labelled second antibody as set forth in Examples 5 and 8. In these and related methods, the amount of bound components are measured to quantify the assay.

In coating the solid support, a procedure is adopted in accordance with the coating characteristic of the immunochemically active material. Most substances will effectively coat by application in solution and incubation for a reasonably brief period. Certain materials, however, such as bacterial suspensions, will not passively adsorb to the solid support, and require a more time-consuming coating procedure whereby the material is allowed to dry on the support surface. In order to reduce nonspecific background staining of the solid support, it may be advisable to apply a blocking agent to the support surface after the initial coating step. In addition the application of the test sample in solution with a buffer and wetting agent, such as PBS/TWEEN, severely reduces nonspecific binding to the solid phase. In the preferred embodiment of enzyme immunoassay for home diagnostic applications, tbe initial coating and blocking stages may be performed in advance of the diagnostic test. The assay kits of such construction exhibit prolonged shelf life of several months with minimal loss of sensitivity.

To establish preferred conditions for coating the solid support, including concentration of reactant, with strength, incubation time, temperature, and pH, preliminary control assays should be conducted with reference reagents, for example with respect to the first antibody in the double antibody-sandwich technique. Control assays are conducted at various antibody concentrations, measuring the color development at each concentration. See Example 3.

Another procedure for quantifying the assays of the invention is conducted to determine the sensitivity to enzyme activity of the given TMB-active solution. These controls should be performed both with the enzyme, and the enzyme-antibody (or antigen) conjugate. Both tests are necessary in that the modified enzyme will characteristically yield an altered enzyme activity. The reaction product (chromophore) is quantitatively measured, using for example a spectrophotometer to measure the absorbance. The specific activity of the various controls is measured by the enzyme dilution required to achieve a given color intensity (see Example 4) or by measuring the initial rate of color development.

The choice of a suitable enzyme preparation for the immunoabsorbent assays of the invention should take a number of factors into account. The enzyme advantageously should be of high purity, and its activity should not be inhibited by the assay technique, immunochemical conjugate and test conditions employed. The enzyme should bind firmly to the molecules to be assayed, or to an intermediary such as biotin.

The enzyme should be a stable material, which exhibits a high specificity and turnover rate for the enzyme chromogenic substrate. Additionally, the sample medium (i.e., urogenital exudate, urine, etc.) should not normally contain the enzyme or its inhibitors. The enzyme should be linked to the antibody or antigen in such a way that each substantially retains its reactivity.

In a single enzyme assay wherein the enzyme used to tag an antibody or antigen catalyzes the chromogenic reaction, suitable enzymes include those classified as oxidoreductase according to the International Union of Biochemists. The more suitable enzymes from this class are those which act on donor groups including —CHOH or —CHNH$_2$ and hydrogen peroxide acceptor.

The enzyme immunoassay techniques of the invention also encompass multiple enzyme systems, which include one or more preliminary stages initially catalyzed by the tagging enzyme. In such multiple enzyme assays, the final chromogenic reaction is catalyzed by an oxidoreductase enzyme. Such multiple enzyme systems may be used, for example, to provide a cascade effect wherein successive stages provide increased turnover of the substrate.

In order to maintain a high signal-to-noise ratio in the colorimetric readings, one should minimize the occurrence of spurious reactions with substances which might commonly be encountered in the test serum, urine, etc. It is desirable for this reason to perform test assays with control samples to determine the background effect of such reactions.

The invention is not intended to be limited to any particular class of antibody used in specific binding to gonococcus antigen, and requires only that the antibody exhibits the requisite degree of specificity for the antigen. If the antigen to be assayed is GC microorganism, the first and second antibodies may be prepared in like manner typically from mouse monoclonal or polyclonal antibody generated from innoculation of mouse or other species with the GC antigen. In this case, the first and second antibodies need not be directed against different binding sites on the antigen molecule. These first and second antibodies may also typically be used interchangeably in the assay. It should also be appreciated that other binding materials such as lectin can be used in place of either the first or second antibody or wherever else antibodies are used in the assay whether to coat the support or to link the assay antigen to enzyme so long as this substance provides desired binding specificity.

The enzyme immunoassay techniques of the invention are further illustrated in the following non-limiting examples in which all proportions are by weight unless otherwise specified:

EXAMPLE 1

An activated TMB solution was prepared by mixing 4.0 parts by volume of reagent (i) with 11.0 parts by volume of reagent (ii), and then adding 0.010 part by volume of the 30 percent hydrogen peroxide solution (reagent (iii)). The mixture was stirred to form a homogenous, activated TMB solution. The individual reagents were produced as follows:

Reagent(i)

Reagent(i) was prepared by dissolving 1.25 g (5.20 mMol) of 3,3′,5,5′-tetramethylbenzidine in 1.00 liter absolute methanol with or without heating. A clear colorless or faintly tan solution resulted which could be stored for at least six weeks in a brown bottle without affecting its usefulness.

Reagent(ii)

Reagent(ii) is a buffer prepared by first dissolving 144.8 grams (1.020 mol) of disodium hydrogen phosphate in 1.00 liter hot deionized water. The phosphate dissolved in the hot deionized water upon stirring. To this solution 102.95 grams (0.4902 mol) of citric acid monohydrate were added. The resulting solution was then diluted to 10.0 liters with additional deionized water, thus forming a citrate-phosphate solution, with a pH of 5.0.

Reagent(iii)

Reagent(iii) consisted of an aqueous solution of hydrogen peroxide, wherein the $H_2O_2$ comprised 30 percent by volume.

EXAMPLE 2

A method of preparing an activated solution containing sulfated tetramethylbenzidine (TMB-s Solution) for use in enzyme linked immunosorbent assays is given as follows:

Sulfated TMB:

Sulfated tetramethylbenzidine was first prepared by dissolving 0.50 grams of tetramethylbenzidine in 55 ml of diethyl ether at room temperature. Fifty microliters of concentrated sulfuric acid was added to this solution, forming immediately a white precipitate of sulfated TMB. The white precipitate of sulfated TMB was separated from the mixture by conventional filtration or decantation. (A further fifty microliters of concentrated sulfuric acid were added to the filtrate; no additional precipitate formed.) The recovered precipitate was then washed twice with fresh ether by mixing the precipitate in the ether for about 30 minutes per elution. The ether mixture was then allowed to dry in air. As the ether evaporated, 30 mg of light tan crystals of sulfated tetramethylbenzidine were recovered. The chemical formula of the resulting sulfated TMB product is not yet established with certainty but is believed to embrace any or all of the following formulas, and most characteristically the first: $TMB \cdot H_2SO_4$, $TMB \cdot 2H_2SO_4$, and $(TMB)_2 \cdot H_2SO_4$.

TMB-s Solution:

An activated solution of sulfated tetramethylbenzidine (TMB-s Solution) was prepared in a similar manner to that set forth in Example 1, except that methanol was not used as a solvent since TMB-s is water soluble.

The activated TMB-s solution was prepared by mixing 5.0 mg of sulfated tetramethylbenzidine (TMB-s) into 1.0 ml of deionized water. Essentially all of the TMB-s dissolved in the deionized water upon mixing, leaving a solution of only slight turbidity. To 0.250 ml of this solution were added 3.5 ml of the citrate-phosphate buffer reagent(ii) of Example 1. After mixing for a short period, there was no visible precipitate. To this mixture was added 25 ml of 3 percent hydrogen peroxide aqueous solution.

The resulting mixture was an activated TMB-s solution ready for use as a chromogenic substance for enzyme linked immunosorbent assays. The total concentration of TMB-S and hydrogen peroxide in this TMB-S solution was equivalent to the concentration of TMB and hydrogen peroxide present respectively for the TMB solution prepared in Example 1.

EXAMPLE 3

Preliminarily to conducting various double-antibody sandwich ELISA's e.g. as in Example 5, the following steps were taken to determine the extent of coating of mouse antibody to the support surface as a function of antibody concentration. Solutions of varying concentrations of the given mouse antibody in suitable buffer such as phosphate buffered saline (PBS) were added to different wells of a polystyrene microtiter plate. The phosphate buffered saline (PBS) contains no calcium and is available from GIBCO Laboratories, Grand Island, N.Y. These solutions were maintained at 23° C.±2° C. for one hour to effect adsorption of the mouse antibody to the support surface. The microtiter plates were then decanted and filled with a blocking solution of 0.5 gm. of bovine serum albumin (BSA Cohn Fraction V, supplied by Sigma Chemical Co., St. Louis, Mo.); 0.02 gms. of sodium azide ($NaN_3$); dissolved in 100 ml of calcium free phosphate buffered saline (PBS). This solution was allowed to remain in the wells for about 30 minutes at 23° C. The solution was decanted and the plates eluted twice with PBS/TWEEN-20 solution. The TWEEN-20 component is polyoxyethylenesorbitan monolaurate available under the tradename Tween-20 from Sigma Chemical Company, St. Louis, Mo.

A suitable dilution (one giving negligible nonspecific binding) of an antibody-horseradish peroxidase conjugate such as goat anti-mouse immunoglobulin*-horseradish peroxidase conjugate was then added to the wells and left to incubate for a period of about 15 minutes to effect specific binding of the conjugate to the mouse antibody.
*Goat antisera generated from innoculation of goat with mouse immunoglobulin.

After elution as above, a fixed quantity of the TMB-s solution of Example 2 was added. The rate of color development of each sample was measured as a function of the coating antibody concentrations to determine which antibody concentrations gave the best color development.

EXAMPLE 4

The following procedure was effected to assay horseradish peroxidase activity with respect to the activated TMB-s solution of Example 2. Twenty microliters of horseradish peroxidase (type VI, from Sigma Chemical Company) was added to a dry polystyrene cuvette. One milliliter of TMB-s activated solution was added to the test tube, which was then incubated at room temperature for 5–10 minutes. The reaction product was measured using a Uvikon 810 spectrophotometer of Kontron, Inc., Redwood City, Calif., recording the absorbance at 660 nanometers (nm). The initial rate of blue color development at 660 nm was directly proportional to the concentration of enzyme. The time period in which such direct proportionality was observed was up to about one minute. Thereafter, the rate of color change tapered off, and maximum color intensity was observed after about 90 minutes.

The above procedure was repeated for various lots of peroxidase comparing their specific activities. The activities of different TMB-s samples may be quantified similarly.

EXAMPLE 5

The following protocol was carried out as a double-antibody sandwich ELISA for gonococcus (GC) bacteria wherein the antigen solution and second antibody were added and incubated simultaneously.

The wells of a polystyrene microtiter plate were passively coated in appropriate dilution with mouse anti-GC (monoclonal antibodies generated by hybridoma using GC membranes or whole cells as antigens) in high ionic strength 0.4M NaCl PBS. The solution was incubated for 1 hour at 37° C. to effect adsorption of the antibody onto the microtiter plate, and the liquid decanted. Remaining adsorption sites were blocked by incubating for 30 minutes with 300 microliters of PBS/0.5% BSA. The blocking agent was decanted, and the wells twice washed with PBS/TWEEN buffer.

Deionized water (having a resistivity of about 18 megaohm cm) was prepared by employing a NANOpure water purification system from the Sybron/Barnstead Company, Boston, Mass. A urogenital (male) sample on calcium alginate swab or endocervical (female) sample on cotton swab was placed in a collection medium composed of 0.5 ml of the deionized water and left to incubate therein for a duration of 4 to 72 hours. The collection medium was not protected from absorption of $CO_2$ from the ambient air. Fifty microliters of concentrated PBS/TWEEN solution (calcium and magnesium free) was then added to the deionized water containing the swab sample and the solution vortexed. The composition of the deionized water collection medium after the PBS/Tween has been added is as follows: Potassium phosphate 0.05 mole per liter, sodium chloride 0.5 mole per liter, and Tween-20 0.1% by volume.

Fifty microliters of the vortexed solution were pipetted to the well along with 5 microliters of mouse anti-GC conjugated to peroxidase (a conjugate of peroxidase and mouse antibody directed against GC antigen). These were mixed using slight agitation, and incubated for two hours at room temperature. The well contents were then decanted, and the well washed thrice using PBS/TWEEN buffer.

One hundred and fifty microliters of activated TMB-s solution, from Example 2, were added and incubated for 30 minutes. The absorbance at 660 nm was then recorded using a Dynatech reader.

The entire immunocomplex attached to the coated surface may be represented schematically by the formula:

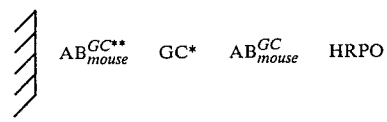

*Antigen being assayed.
**$AB_x^y$ = antibody to y raised in animal x.

* Antigen being assayed.
** $AB_x^y$ = antibody to y raised in animal x.

The protocol set forth in Example 5 was successfully used to detect gonococcal concentration levels as low as 5,000 cells per milliliter.

EXAMPLE 6

The double antibody sandwich ELISA for GC of Example 5 was repeated with the following modification, to effect a sequential assay:

Deionized water (having a resistivity of about 18 megaohm cm) was prepared by employing a NANOpure water purification system from the Sybron/Barnstead Company, Boston, Mass. A urogenital (male) on calcium alginate swab or endocervical (female) sample on cotton swab was placed in a collection medium composed of 0.5 ml of the deionized water and left to incubate therein for a duration of 4 to 72 hours. The collection medium was not protected from absorption of $CO_2$ from ambient air. Fifty microliters of concentrated PBS/TWEEN solution (calcium and magnesium free) was then added to the deionized water containing the swab sample and the solution vortexed. The composition of the deionized water collection medium after the PBS/Tween has been added is as follows: Potassium phosphate 0.05 mole per liter, sodium chloride 0.5 mole per liter, and Tween-20 0.1% by volume.

Fifty microliters of the vortexed solution were pipetted to the wells, precoated in the manner set forth in Example 5 with monoclonal mouse anti GC. This was incubated for 2 hours at 37° C., decanted, and the wells thrice washed with PBS/TWEEN buffer.

Fifty microliters of peroxidase-conjugated mouse anti-GC (peroxidase conjugated to mouse antibody directed against GC antigen) was then added in an appropriately diluted solution with PBS/BSA/Tween (0.5 gms. BSA per 100 ml PBS and 0.1 ml Tween). This solution was incubated for 30 minutes at room temperature, decanted, and the wells eluted as above.

The nonsimultaneous double sandwich ELISA for GC of Example 6 was used successfully for the detection of gonococcal cells at concentrations of 50,000 cells/ml.

The assay protocol for Example 6 was repeated except that the collection medium for the swab sample was a solution of PBS/TWEEN instead of deionized water. When the PBS/TWEEN collection medium was used, gonococcal cells could not be as reliably detected at low concentrations approaching about 50,000 cells/ml.

EXAMPLE 7

The following protocol was effected to assay for antibody directed against gonococcus bacteria:

Individual wells of polyvinyl chloride microtiter plates were coated with 50 microliters solution of GC suspended in deionized water. The deionized water (having a resistivity of about 18 megaohm cm) was prepared by employing a Sybron/Barnstead NANOpure water purification system and the GC sample used in the suspension was harvested from culture plates in conventional manner utilizing a Thayer-Martin culture medium. The GC suspension was allowed to dry overnight at 37° C. and/or dried in a dessicator for 1-2 hours and then fixed by adding 300 microliters of methanol to each well for 10 minutes. Each well was then twice washed using PBS/TWEEN buffer, blocked by incubating 30 minutes at room temperature with 300 ml per well of PBS/0.5% BSA/0.02% sodium azide. The wells were then washed twice with PBS/TWEEN.

Fifty microliters of mouse anti-GC bacteria were added to each well in appropriate dilution. This was obtained from spent cell culture fluid containing antibody secreted by mouse hybridoma cells or from ascites fluid or from polyclonal rabbit serum. The antibody solution was incubated for 1 hour at room temperature, and thrice washed with PBS/TWEEN buffer.

One hundred microliters of peroxidase conjugated goat anti-mouse Ig was added in solution with PBS/BSA/Tween, appropriately diluted. The solution was incubated for 30 minutes to 1 hour, then thrice washed with PBS/Tween.

One hundred and fifty microliters of activated TMB solution, prepared in accordance with Example 1, were added and incubated for 30 minutes, after which an absorbance reading at 660 nm was recorded with a Dynatech reader from Dynatech Laboratories, Alexandria, Va.

The foregoing protocol was used successfully to detect mouse anti-GC at concentrations as low as 800 nanograms/ml.

The entire immunocomplex attached to the coated surface may be represented schematically by the formula:

$$GC \quad * \quad Ab_{mouse}^{GC} \quad Ab_{goat}^{mouse} \quad HRPO$$

*Antigen being assayed.

\* Antigen being assayed.

EXAMPLE 8

The following preferred protocol was carried out as a double-antibody sandwich ELISA for gonococcus (GC) bacteria wherein the antigen and second antibody were added and incubated simultaneously.

Precoated polystyrene tubes were prepared by passively coating monoclonal antibody raised against GC membranes appropriately diluted in high ionic strength 0.4M NaCl PBS solution. The solution was incubated for about 1 hour at room temperature to effect adsorption of the antibody onto the tube surface, and the remaining liquid decanted. The remaining adsorption sites were blocked by incubating for 30 minutes with 3 ml solution of PBS/0.5% BSA/20% sucrose (wt./vol.). The blocking agent was aspirated and the tubes air dried without prewashing with buffer.

A urogenital (male) or endocervical (female) sample on calcium alginate or cotton swab was placed in a vial containing 0.5 ml of deionized water (having a resistivity of about 18 megaohm cm) prepared by employing a NANOpure water purification system from Sybron/Barnstead Company, Boston, Mass. The swab sample was left to incubate in the deionized water for a period of between about 0.5 to 24 hours. The deionized water was not protected from absorption of $CO_2$ from the ambient air.

Fifty microliters of a concentrated PBS-Tween 20 buffuer solution (calcium and magnesium free) was then added to the vial containing the sample in the deionized water and the vial contents vigorously shaken by hand. The composition of the deionized water collection medium after the PBS/Tween has been added is as follows: Potassium phosphate 0.05 mole per liter, sodium chloride 0.5 mole per liter, and Tween-20 0.1% by volume.

One hundred eighty microliters of the sample solution with PBS-TWEEN buffer admixed therein was then removed from the vial by pipet and placed in the polystyrene tube that has been precoated with monoclonal antibody raised against GC membranes.

Twenty microliters of mouse anti-GC conjugated to peroxidase were then immediately added to the tube. The tube was capped, and the sample and conjugated antibody mixed by inversion. The tube contents were allowed to incubate at room temperature for about two hours. The contents were then decanted and the tube washed three times with tap water.

Five hundred microliters of activated TMB-s solution as prepared in accordance with Example 2 were added to the tube contents and the resulting mixture allowed to incubate for about 15 minutes. Three hundred microliters of mixture were then removed from the tube and placed in a well of a microtiter plate whereupon the absorbance at 660 nanometers was measured using a Dynatech Microelisa MR 580 Autoreader.

The protocol set froth in Example 8 employing either urogenital (male) or endocervical (female) swab samples was successfully used to detect gonococcal concentrations as low as about 5,000 gonococcal cells per milliliter.

The assay methods set forth in the illustrative examples 5–8 may be applied in a home or clinical diagnostic assay kit for detection of gonorrhea. For example, a number of vials containing the various immunologic reagents required for the assay may be included in a kit. The user need then only mix these reagents with the test sample in accordance with a given protocol and await a color change in the final solution. One method of application of the double antibody sandwich ELISA to a home diagnostic kit for detection of gonorrhoea could be effected, illustratively, by providing the kit with one vial (vial 1), which has been precoated with a first antibody and blocking solution and a second vial (vial 2) which would contain a solution of the second antibody—enzyme conjugate in phospate buffered saline/Tween. Another vial (vial 3) could contain a solution of the chromogen and solvent, and an additional vial (vial 4) could contain the solution of buffer and hydrogen peroxide. A vial (vial 5) could contain the deionized water collection medium. In carrying out the assay, the user or a clinician need first collect a urogenital (male) or endocervical (female) swab sample of specimen suspected of containing gonococcus bacteria. The user may immerse the swab with sample specimen thereon in the deionized water collection medium (vial 5) and allow it to incubate for at least about 15 minutes to about 3 to 4 hours, whereupon the contents of vial 5 could be transferred to vial 2. The contents of vial 2 would be immediately transferred to vial 1 and the contents therein allowed to incubate for a prescribed period at room temperature. The user could thereupon discard the liquid contents in vial 1 and rinse the remaining contents several times with cold tap water. The contents in vial 4 could then be mixed into the contents of vial 3 to form an activated chromogenic solution in vial 3. The user could then easily transfer the activated chromogenic solution from vial 3 to vial 1 whereupon the user could wait another prescribed period of time and then observe whether the contents of vial 1 have developed a blue color, thus confirming the presence of the antigen being assayed.

It should be appreciated that the foregoing procedure is merely illustrative. The deionized water collection medium for gonococcus specimen although advantageously used for immersion of a urogenital or endocervical swab sample is not limited to such use. The specimen could be collected by other than use of swab, and then immersed in the collection medium. Also, the deionized water collection medium is not limited to use with the chromogehic compound of the invention, but may be used in any colorimetric immunoassay with any other suitable chromogen. However, heightened sensitivity occurs when the assay is conducted through use of both deionized water collection medium and chromogenic compound of the invention.

Although the preferred application of the chromogenic compound of the invention has been illustrated in the foregoing detailed description in the context of certain specific enzyme linked immunosorbent assays, it should be appreciated that the chromogen is equally applicable to any type of enzyme immunoassay. Accordingly, the invention is not intended to be limited to the specific embodiments or examples set forth in the specification, but rather is defined by the claims and equivalents thereof.

We claim:

1. An enzyme immunoassay for the colorimetric detection of an antigen selected from the group consisting of microorganisms and antigenic derivatives of microorganisms, said enzyme immunoassay of the type wherein a biological material comprising said antigen is collected in a collection medium forming a biological sample; a conjugate is formed between an antibody and enzyme, said conjugate is admixed with the sample to be tested for the antigen, said antigen binds with the conjugate to form an antigent/antibody complex in solid phase, the enzyme of the conjugate being bound in the antigen/antibody complex in solid phase, and the presence of said antigen is determined by measuring the activity of said enzyme with a chromogenic substrate, wherein the improvement comprises:

immersing the biological material comprising said antigen in a collection medium consisting of deionized water to form said biological sample, the deionized water deionized to a purity yielding a resistivity of the water of at least 1 megaohm cm; and maintaining the biological material immersed in said collection medium consisting of deionized water for an immersion period of at least about 15 minutes without adding other reagents to the biological sample during said immersion period, the biological sample permissibly exposed to the atmosphere during the immersion period.

2. An enzyme immunoassay as in claim 1 wherein the deionized water is deionized to a purity yielding a resistivity of at least 10 megohm cm.

3. An enzyme immunoassay as in claim 1 wherein the deionized water is deionized to a purity yielding a resistivity of between about 10 megaohm cm and 20 megaohm cm.

4. An enzyme immunoassay as in claim 1 further comprising the step of collecting the biological material on a collection member from a subject to be tested for said biological material prior to immersing said biological material in the collection medium.

5. An enzyme immunoassay as in claim 4 wherein the collection member comprises a clinical swab of a material selected from the group consisting of calcium alginate and cotton.

6. An enzyme immunoassay as in claim 1 wherein the immersion period for the biological material in the collection medium is at least one-half hour.

7. An enzyme immunoassay as in claim 1 further comprising the step of admixing into the biological sample at the end of the immersion period a phosphate-buffered saline solution essentially free of calcium and magnesium, said phosphate-buffered saline solution comprising potassium phosphate and sodium chloride.

8. An enzyme immunoassay as in claim 7 wherein the phosphate-buffered saline solution further comprises a detergent.

9. An enzyme immunoassay as in claim 1 wherein the presence of said biological material is determined visually.

10. An enzyme immunoassay for the colorimetric detection of an antigen selected from the group consisting of microorgansims and antigenic derivatives of microorganisms, said enzyme immunoassay of the type wherein a biological material comprising said antigen is collected in a collection medium forming a biological sample; a quantity of a first antibody is adsorbed to a solid support; a conjugate is formed is between a second antibody and an enzyme, said conjugate is admixed with the biological sample to be tested for the antigen, said antigen in the sample binds to said first antibody and to said conjugate to form an antigen/antibody complex in solid phase; and the presence of said antigen is determined by measuring the activity of the enzyme in the antigen/antibody complex with a chromogenic substrate, wherein the improvement comprises:

(a) immersing the biological material comprising said antigen in a collection medium consisting of deionized water to form said biological sample, the deionized water deionized to a purity yielding a resistivity of the water of at least 1 megaohm cm; and (b) maintaining the biological material immersed in said collection medium consisting of said deionized water for an immersion period of at least 15 minutes without adding other reagents to the biological sample during said immersion period, the biological sample permissibly exposed to the atmosphere during said immersion period.

11. An enzyme immunoassay as in claim 10 wherein the deionized water is deionized to a purity yielding a resistivity of at least 10 megaohm cm.

12. An enzyme immunoassay as in claim 10 wherein the deionized water is deionized to a purity yielding a resistivity of between about 10 megaohm cm and 20 megaohm cm.

13. An enzyme immunoassay as in claim 10 further comprising the step of collecting the biological material on a collection member from a subject to be tested for said antigen prior to immersing said biological material in the collection medium.

14. An enzyme immunoassay as in claim 13 wherein the collection member comprises a clinical swab of a material selected from the group consisting of calcium alginate and cotton.

15. An enzyme immunoassay as in claim 10 wherein the immersion period for the biological material in the collection medium is at least one-half hour.

16. An enzyme immunoassay as in claim 10 comprising the step of admixing into the biological sample at the end of the immersion period a phosphate-buffered saline solution essentially free of calcium and magnesium, said phosphate-buffered saline solution comprising potassium phosphate and sodium chloride.

17. An enzyme immunoassay as in claim 16 wherein the phosphate-buffered saline solution further comprises a detergent.

18. An enzyme immunoassay as in claim 10 wherein the antigen is selected from the group consisting of gonococcus bacteria and antigenic derivatives of gonococcus.

19. An enzyme immunoassay for the colorimetric detection of antigen selected from the group consisting of gonococcus bacteria and antigenic derivatives of gonococcus comprising the steps of:

(a) adsorbing a quantity of a first antibody onto a solid support;

(b) forming a conjugate between a second antibody and an enzyme;

(c) immersing a biological material comprising said antigen in a collection medium consisting of deionized water to form a biological sample, the deionized water deionized to a purity yielding a resistivity of the water of at least 1 megaohm cm;

(d) maintaining the biological material immersed in the collection medium consisting of deionized water for an immersion period of at least 15 minutes without adding other reagents to the biological sample during said immersion period, the biological sample permissibly exposed to the atmosphere during said immersion period;

(e) admixing the biological sample with the conjugate after the immersion period in step (d); and (f) immersing the solid support with first antibody adsorbed thereon into the mixture of biological sample and conjugate from step (e) said antigen in the sample binding to the first antibody and said conjugate to form an antigen-antibody complex in solid phase and determining the presence of said antigen by measuring the activity of said enzyme of the antigen/antibody complex with a chromogenic substance substrate.

20. An enzyme immunoassay as in claim 19 wherein the deionized water is deionized to a purity yielding a resistivity of at least 10 megaohm cm.

21. An enzyme immunoassay as in claim 19 wherein the deionized water is deionized to a purity yielding a resistivity of between about 10 megaohm cm and 20 megaohm cm.

22. An enzyme immunoassay as in claim 19 wherein the immersion period for the biological material in the collection medium is at least one-half hour.

23. An enzyme immunoassay as in claim 19 further comprising the step of collecting the biological material on a collection member comprising a clinical swab of a material selected from the group consisting of calcium alginate and cotton prior to immersing said biological material in the collection medium and thence immersing said collection member and biological material thereon into the collection medium.

24. An enzyme immunoassay an in claim 19 further comprising the step of admixing into the biological sample after the immersion period a phosphate-buffered saline solution essentially free of calcium and magnesium.

* * * * *